United States Patent
Lortz et al.

(10) Patent No.: US 10,920,084 B2
(45) Date of Patent: Feb. 16, 2021

(54) METAL OXIDE-CONTAINING DISPERSION WITH HIGH SALT STABILITY

(71) Applicants: Wolfgang Lortz, Wächtersbach (DE); Ulrich Fischer, Mömbris (DE); Daniel Ness, Hanau (DE); Gabriele Bergmann, Grosskrotzenburg (DE); Katharina Dauth, Offenbach (DE)

(72) Inventors: Wolfgang Lortz, Wächtersbach (DE); Ulrich Fischer, Mömbris (DE); Daniel Ness, Hanau (DE); Gabriele Bergmann, Grosskrotzenburg (DE); Katharina Dauth, Offenbach (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 15/743,242

(22) PCT Filed: Jun. 28, 2016

(86) PCT No.: PCT/EP2016/064955
§ 371 (c)(1),
(2) Date: Jan. 9, 2018

(87) PCT Pub. No.: WO2017/009032
PCT Pub. Date: Jan. 19, 2017

(65) Prior Publication Data
US 2018/0194947 A1    Jul. 12, 2018

(30) Foreign Application Priority Data
Jul. 10, 2015 (EP) ..................... 15176283

(51) Int. Cl.
| | | |
|---|---|---|
| C09C 1/40 | (2006.01) | |
| C09C 1/30 | (2006.01) | |
| C01B 33/14 | (2006.01) | |
| C01B 33/141 | (2006.01) | |
| C01B 33/159 | (2006.01) | |
| C01B 33/149 | (2006.01) | |
| C09C 1/36 | (2006.01) | |
| C09C 1/24 | (2006.01) | |
| A61K 8/04 | (2006.01) | |
| A61K 8/26 | (2006.01) | |
| A61K 9/10 | (2006.01) | |
| C09D 17/00 | (2006.01) | |
| C11D 7/20 | (2006.01) | |
| C11D 17/00 | (2006.01) | |
| D21H 19/42 | (2006.01) | |
| C09C 3/06 | (2006.01) | |

(52) U.S. Cl.
CPC .............. *C09C 1/405* (2013.01); *A61K 8/044* (2013.01); *A61K 8/26* (2013.01); *A61K 9/10* (2013.01); *C01B 33/14* (2013.01); *C01B 33/149* (2013.01); *C01B 33/1417* (2013.01); *C01B 33/159* (2013.01); *C09C 1/24* (2013.01); *C09C 1/309* (2013.01); *C09C 1/3045* (2013.01); *C09C 1/3054* (2013.01); *C09C 1/3063* (2013.01); *C09C 1/3081* (2013.01); *C09C 1/3661* (2013.01); *C09C 1/3684* (2013.01); *C09C 1/3692* (2013.01); *C09C 1/407* (2013.01); *C09C 3/063* (2013.01); *C09D 17/001* (2013.01); *C09D 17/007* (2013.01); *C11D 7/20* (2013.01); *C11D 17/0013* (2013.01); *D21H 19/42* (2013.01); *C01P 2004/61* (2013.01); *C01P 2004/62* (2013.01); *Y10S 977/773* (2013.01)

(58) Field of Classification Search
None
See application file for complete search history.

(56) References Cited

U.S. PATENT DOCUMENTS

| | | | |
|---|---|---|---|
| 5,981,131 A | 11/1999 | Hirama et al. | |
| 6,036,808 A * | 3/2000 | Shaw-Klein | B41M 5/0355 347/105 |

(Continued)

FOREIGN PATENT DOCUMENTS

| | | |
|---|---|---|
| WO | WO 02/22745 | 3/2002 |
| WO | WO 2004/035474 | 4/2004 |

(Continued)

OTHER PUBLICATIONS

Google Patents. English translation of WO 2009/119178 A1. https://patents.google.com/patent/WO2009119178A1/en accessed Oct. 4, 2018, originally published Oct. 1, 2009, 21 printed pages. (Year: 2009).*

(Continued)

*Primary Examiner* — Isaac Shomer
(74) *Attorney, Agent, or Firm* — Law Office of: Michael A. Sanzo, LLC

(57) ABSTRACT

Aqueous dispersion containing a hydrophilic metal oxide powder comprising a metal oxide and a surface modification of the metal oxide, wherein a) the metal oxide is selected from the group consisting of $TiO_2$, $ZrO_2$, $SiO_2$, $Al_2O_3$, $Fe_2O_3$, $Fe_3O_4$, $Sb_2O_3$, $WO_3$, $CeO_2$ and mixed oxides thereof and b) the surface modification
  b1) comprises silicon atoms and aluminum atoms and
  b2) the silicon atoms are at least partly bonded to a hydrocarbon radical via a C atom and
  b3) the Al/Si molar ratio of the surface modification is 1:2-1:20.

16 Claims, No Drawings

(56) References Cited

U.S. PATENT DOCUMENTS

| | | | |
|---|---|---|---|
| 8,017,098 B2 | 9/2011 | Uhrlandt et al. | |
| 8,885,341 B2 | 11/2014 | Desmarets | |
| 8,911,638 B2 | 12/2014 | Lortz | |
| 8,980,784 B2 | 3/2015 | Schultz Isfort et al. | |
| 10,144,858 B2 | 12/2018 | Kennedy | |
| 10,723,628 B2* | 7/2020 | Lortz | C01B 33/159 |
| 10,767,103 B2 | 9/2020 | Lortz et al. | |
| 2002/0121156 A1* | 9/2002 | Menzel | B82Y 30/00 75/255 |
| 2002/0168312 A1 | 11/2002 | Mangold et al. | |
| 2002/0172827 A1 | 11/2002 | O'Connor et al. | |
| 2003/0185739 A1 | 10/2003 | Mangold et al. | |
| 2003/0220204 A1 | 11/2003 | Baran et al. | |
| 2004/0037964 A1 | 2/2004 | Davies et al. | |
| 2004/0241101 A1 | 12/2004 | Baran et al. | |
| 2005/0133766 A1 | 6/2005 | Barthel et al. | |
| 2005/0282935 A1 | 12/2005 | Christian | |
| 2006/0093541 A1* | 5/2006 | Uhrlandt | C01B 33/193 423/335 |
| 2006/0134606 A1* | 6/2006 | Montagu | G01N 33/544 435/5 |
| 2007/0110906 A1 | 5/2007 | Edelmann et al. | |
| 2009/0301345 A1 | 12/2009 | Mangold et al. | |
| 2010/0092765 A1 | 4/2010 | Hager et al. | |
| 2010/0107930 A1 | 5/2010 | Lortz et al. | |
| 2010/0181525 A1* | 7/2010 | Belmont | B82Y 30/00 252/79.1 |
| 2010/0288963 A1 | 11/2010 | Mitina et al. | |
| 2010/0301264 A1 | 12/2010 | Mangold et al. | |
| 2011/0028662 A1* | 2/2011 | Wiesner | A61K 49/0032 525/478 |
| 2011/0118382 A1* | 5/2011 | Reichenbach-Klinke | C04B 40/0039 523/130 |
| 2011/0245391 A1* | 10/2011 | Karpov | C08K 9/10 524/262 |
| 2013/0071649 A1 | 3/2013 | Hager et al. | |
| 2013/0303361 A1 | 11/2013 | Schultz Isfort et al. | |
| 2014/0292951 A1* | 10/2014 | Ferrar | B41M 5/502 347/73 |
| 2015/0075798 A1 | 3/2015 | Tang et al. | |
| 2015/0159074 A1 | 6/2015 | Luyster | |
| 2017/0151136 A1 | 6/2017 | Kim | |
| 2017/0166805 A1 | 6/2017 | Schultheiss | |
| 2018/0312741 A1 | 11/2018 | Lortz et al. | |
| 2019/0106328 A1 | 4/2019 | Lortz et al. | |
| 2019/0127587 A1 | 5/2019 | Lortz et al. | |

FOREIGN PATENT DOCUMENTS

| | | | | |
|---|---|---|---|---|
| WO | WO 2008/071462 | | 6/2008 | |
| WO | WO-2009119178 A1 * | | 10/2009 | C01B 33/149 |
| WO | WO 2010/042672 | | 4/2010 | |
| WO | WO 2014/020061 | | 2/2014 | |
| WO | WO 2017/071985 | | 5/2017 | |

OTHER PUBLICATIONS

Z Zhang, AE Berns, S Willbold, J Buitenhuis. "Synthesis of poly(ethylene glycol) (PEG)-grafted colloidal silica particles with improved stability in aqueous solvents." Journal of Colloid and Interface Science, vol. 310, 2007, pp. 446-455. (Year: 2007).*
Grace Davison Engineered Materials. "LUDOX® Colloidal Silica in Coatings Lithium Polysilicate in Coatings." Obtained from https://grace.com/coatings-and-inks/en-us/Documents/LUDOX%20Coatings%20TI.pdf on Oct. 4, 2018. pp. 1-6. (Year: 2018).*
Sigma-Aldrich. Ludox CL Colloidal Silica. https://www.sigmaaldrich.com/catalog/product/aldrich/420883?lang=en&region=US accessed Jan. 8, 2019, 3 printed pages. (Year: 2019).*
Sigma-Aldrich. Ludox CL-X Colloidal Silica. https://www.sigmaaldrich.com/catalog/product/aldrich/420891?lang=en&region=US accessed Jan. 8, 2019, 3 printed pages. (Year: 2019).*

CA Hall. "Deposition of Aluminium Oxide Modified Core-shell Silica Particles onto Silica Surfaces." Thesis, University of Manchester , 2010, pp. 1-90. (Year: 2010).*
YC Park et al. "Effect of PEG molecular weight on stability, T2 contrast, cytotoxicity,and cellular uptake of superparamagnetic iron oxide nanoparticles (SPIONs)." Colloids and Surfaces B: Biointerfaces, vol. 119, 2014, pp. 106-114. (Year: 2014).*
Pamela M. Visintin, Ruben G. Carbonell, Cynthia K. Schauer, and Joseph M. DeSimone. "Chemical Functionalization of Silica and Alumina Particles for Dispersion in Carbon Dioxide." Langmuir 2005, 21, pp. 4816-4823. (Year: 2005).*
English translation of the International Search Report for PCT/EP2016/074923 filed Oct. 18, 2016 for copending U.S. Appl. No. 15/770,786.
English translation of the Written Opinion of the International Searching Authority for PCT/EP2016/074923 filed Oct. 18, 2016 for copending U.S. Appl. No. 15/770,786.
English translation of the International Preliminary Report on Patentability for PCT/EP2016/074923 filed Oct. 18, 2016 for copending U.S. Appl. No. 15/770,786.
Aurand, et al., "Comparison of Oil Recovery for Six Nanofluids in Berea Sandstone Cores," International Symposium of the Society of Core Analysts, Avignon, France, Sep. 8, 2011.
Hendraningrat, et al., "A Coreflood Investigation of Nanofluid enhanced Oil Recovery in Low-Medium Permeability Berea Sandstone," SPE 164106:1-14 (Apr. 2013).
Ibrahim, et al., "Understanding the Mechanism of Nanoparticles Applications in Enhanced Oil Recovery," SPE 175806-MS:1-19 (Apr. 2015).
McElfresh, et al., "Stabilizing Nano Particle Dispersions in High Salinity, High Temperature Downhole Environments," SPE 154758:1-6 (Jan. 2012).
Roustaei, et al., "An evaluation of modified silica nanoparticles' efficiency in enhancing oil recovery of light and intermediate oil reservoirs," Egyptian Journal of Petroleum 22:427-433 (Dec. 2013).
Vuorinen, et al., "Thermooxidative degradation of LDPE nanocomposites: Effect of surface treatments of fumed silica and boehmite alumina," Polymer Degradation and Stability 98(11)2297-2305 (Aug. 2013).
U.S. Appl. No. 15/770,786, filed Apr. 25, 2018, Lortz.
English translation of the International Search Report for PCT/EP2016/0649655filed Jun. 28, 2016.
English translation of the Written Opinion of the International Searching Authority for PCT/EP2016/064955 filed Jun. 28, 2016.
English translation of the International Preliminary Report on Patentability for PCT/EP2016/064955 filed Jun. 28, 2016.
English translation of the International Search Report for PCT/EP2016/064966 filed Jun. 28, 2016 for copending U.S. Appl. No. 15/743,177.
English translation of the Written Opinion of the International Searching Authority for PCT/EP2016/064966 filed Jun. 28, 2016 for copending U.S. Appl. No. 15/743,177.
English translation of the International Preliminary Report on Patentability for PCT/EP2016/064966 filed Jun. 28, 2016 for copending U.S. Appl. No. 15/743,177.
English translation of the International Search Report for PCT/EP2016/064994 filed Jun. 28, 2016 for copending U.S. Appl. No. 15/743,214.
English translation of the Written Opinion of the International Searching Authority for PCT/EP2016/064994 filed Jun. 28, 2016 for copending U.S. Appl. No. 15/743,214.
English translation of the International Preliminary Report on Patentability for PCT/EP2016/064994 filed Jun. 28, 2016 for copending U.S. Appl. No. 15/743,214.
Metin. et al., "Stability of Aqueous Silica Nanoparticle Dispersions under Subsurface Conditions," Clean Technology www.ct-si.org, ISBN 978-1-4398-3419-0 pp. 25-28 (2010).
Gonzalez-Matheus, et al., "Pickering-Stabilized Latexes with High Silica Incorporation and Improved Salt Stability," Part. Part. Syst. Charact. 31:94-100 (2014).
U.S. Appl. No. 15/743,214, filed Jan. 9, 2018, Lortz.
U.S. Appl. No. 15/743,177, filed Jan. 9, 2018, Lortz.

(56) References Cited

OTHER PUBLICATIONS

Restriction Requirement dated Apr. 4, 2019 for copending U.S. Appl. No. 15/743,214.
Response to Restriction Requirement for copending U.S. Appl. No. 15/743,214, filed Jun. 29, 2019.
Office Action for copending U.S. Appl. No. 15/743,214, dated Sep. 17, 2019.
Office Action for copending U.S. Appl. No. 15/743,177, dated Dec. 10, 2019.
Amendment and Response for copending U.S. Appl. No. 15/743,214, filed Dec. 17, 2019.
AEROSIL® R 816, Product Information; pp. 1-2; Oct. 2019.
Gelest Silane Coupling Agents: Connecting Across Boundaries; (2006); www.gelest.com.
Ludox® Technical Literature; E.I. du Pont de Nemours & Company, (1999).
Office Action for copending U.S. Appl. No. 15/770,786, dated Oct. 3, 2019.
Amendment and Response for copending U.S. Appl. No. 15/770,786, filed Jan. 3, 2020.
Final Office Action for copending U.S. Appl. No. 15/743,214, dated Jan. 7, 2020.
Amendment and Response for copending U.S. Appl. No. 15/743,177, filed Mar. 12, 2020.
Notice of Abandonment for copending U.S. Appl. No. 15/743,214, dated Mar. 17, 2020.
Notice of Allowance for copending U.S. Appl. No. 15/743,177, dated Mar. 23, 2020.
Notice of Allowance for copending U.S. Appl. No. 15/770,786, dated Apr. 14, 2020.

\* cited by examiner

METAL OXIDE-CONTAINING DISPERSION WITH HIGH SALT STABILITY

CROSS REFERENCE TO RELATED APPLICATIONS

The present application is US national stage of international application PCT/EP2016/064955, which had an international filing date of Jun. 28, 2016, and which was published in German under PCT Article 21(2) on Jan. 19, 2017. Priority is claimed to European application EP 15176283.8, filed on Jul. 10, 2015.

The invention relates to metal oxide-containing dispersions having high salt stability and to the preparation and use thereof.

Improving the stability of aqueous silicon dioxide dispersions is a subject of research. Attempts are commonly made to protect the dispersion from sedimentation and reagglomeration by providing the silicon dioxide particles with appropriate surface modification.

Thus, for example, US2004241101 discloses a stable pharmaceutical dispersion which contains silicon dioxide particles surface-modified with polyethylene glycols. The latter may be obtained, for example, by reacting an ammonia-stabilized colloidal silicon dioxide with a polyethoxylated trialkoxysilane.

US2002172827 is concerned inter alia with production of redispersible, nanoscale silicon dioxide particles. This involves coating a negatively charged silica sol with an aluminum oxide. Sodium dodecylbenzenesulphonate is then added as a surface-modifying agent.

WO2004035474 claims a process for producing a stable aqueous dispersion obtained by mixing silanized, colloidal silicon dioxide particles with an organic binder. The silanizing agent is for example a glycidylepoxysilane. The organic binder may be a polyethylene glycol.

In Part. Syst. Charact. 2014, 31, 94-100 colloidal silicon dioxide particles are surface-modified with 2-[methoxy(polyethyleneoxy)propyl]trimethoxysilane to increase salt stability. Clean Technology, www.ct-si.org, ISBN 978-1-4398-3419-0 (2010) 25-28 also addresses salt stability.

WO03/106339 describes a precipitated silica having a BET surface area of 150-400 $m^2/g$, a CTAB surface area of 140-350 $m^2/g$ and an $Al_2O_3$ content of 0.2-5 wt %. This silica may be modified with a multiplicity of silanes and result in both hydrophilic and hydrophobic products. The ratio of silane to precipitated silica may also be varied within wide limits, namely 0.5 to 50 parts of silane based on 100 parts of precipitated silica. The reaction may be effected in the dispersion of the precipitated silica with subsequent drying and heat treatment. Conditions in this regard are not recited and the properties of the dispersion are not further specified WO02/22745 discloses a process for primer coating of steel in which an aqueous aluminum oxide-silicon dioxide sol comprising 0.05-2.0 wt % of aluminum oxide is employed.

The aluminum oxide-silicon dioxide sol may contain a silane coupling agent having alkoxysilane groups and an organic radical having a functional group, such as an amino, epoxide or isocyanate.

WO2010/042672 discloses a coating composition for thermoplastic and thermosetting substrates, comprising an aqueous dispersion having a pH of less than 7.5. Said composition contains surface-modified silicon dioxide nanoparticles having a median particle diameter of 40 nm or less, an alkoxysilane oligomer and a silane coupling agent.

Suitable surface-modifying agents are those having a radical that can react with the silanol groups on the silicon dioxide surface and having a hydrophilic radical, for example an acid radical, an ammonium radical, a polyoxyethylene radical or a hydroxyl group.

However it has been found that for many applications the salt stability achieved is insufficient. It is accordingly an object of the present invention to provide a dispersion having improved salt stability. It is a further object of the invention to provide a process for producing this dispersion.

The invention provides an aqueous dispersion containing a hydrophilic metal oxide powder comprising a metal oxide and a surface modification of the metal oxide, wherein
a) the metal oxide is selected from the group consisting of $Al_2O_3$, $CeO_2$, $Fe_2O_3$, $Fe_3O_4$, $Sb_2O_3$, $SiO_2$, $TiO_2$, $WO_3$, $ZrO_2$ and mixed oxides thereof and
b) the surface modification
  b1) comprises silicon atoms and at least one metal atom M selected from the group consisting of Al, Ti and Zr, Al is preferred,
  b2) are at least partly bonded to a hydrocarbon radical via a C atom and
  b3) the M/Si molar ratio of the surface modification is 1:2-1:20.

The metal oxide may preferably be obtained from pyrogenic processes. Here, metal compounds are converted in a flame generated by the reaction of hydrogen and oxygen. The thus obtained powders are referred to as "pyrogenic" or "fumed". The reaction initially forms highly disperse primary particles, which in the further course of reaction coalesce to form aggregates. The aggregate diameters of these powders are generally in the range of 0.2-1 μm. Said powders may be converted into the nm range advantageous for the present invention by suitable grinding and subsequently treated with the surface-modifying agent.

The term "mixed oxide" is to be understood as meaning an intimate mixture of the mixed oxide components metal $M_1$ and metal $M_2$ at the atomic level, at which the particles may also have $M_1$-O-$M_2$-bonds.

"Surface-modified" is to be understood as meaning that the silica on its surface bears groups which very largely give the particles the hydrophilic properties exhibited by the unmodified silica. This causes the aqueous dispersion to remain stable. The term "stable" is to be understood as meaning that no appreciable re-agglomeration, and thus no sedimentation, occurs. In an aqueous solution hydrophobized particles would reagglomerate and separate in a very short time.

This stability is to be retained even for aqueous solutions having a high salt concentration and at elevated temperatures. For the dispersion of the present invention a 0.5 weight percent dispersion in a reference solution simulating seawater is stable for at least one week at a temperature of 90° C. Testing of stability is performed in a three percent NaCl solution.

A suitable analytical method for detecting the surface elements and their bonds is X-ray photoelectron spectroscopy (XPS). A depth profile may be generated by stepwise sputter etching. Additional information about the composition of the surface can be determined via energy-dispersive x-ray radiation (TEM-EDX). The composition of the total particle may be determined by chemical or physicochemical methods, for example x-ray fluorescence analysis.

Good results in terms of salt stability are obtained with aluminum-containing mixed oxides. Particularly preferred are mixed aluminum-silicon oxides, very particularly those where the $Al_2O_3/SiO_2$ weight ratio in the surface-modified metal oxide powder is 0.1:99.9-5:95, in particular 0.2:99.8-3:97.

The $Al_2O_3/SiO_2$ weight ratio at the surface may be greater, smaller or equal to the weight ratio in the total particle. The term "ttl." corresponds to the weight ratio in the total particle. An $(Al_2O_3/SiO_2)_{surface}/(Al_2O_3/SiO_2)_{ttl}$ ratio of 0.1-10 is preferred. The weight ratio at the surface may be determined for example by x-ray-induced photoelectron spectroscopy (XPS) analysis of the powder. The weight ratio in the total particle may be determined by chemical or physicochemical methods, for example X-ray fluorescence analysis.

In the dispersion according to the invention the proportion of water is preferably 50-90 wt % and of surface-modified metal oxide powder is preferably 10-50 wt %. Depending on the planned further use, the proportion of surface-modified metal oxide powder may be reduced further.

The liquid phase may contain small proportions of alcohol, such as methanol, ethanol, propanol or butanol, in addition to water. The proportion of alcohol is generally less than 1 wt % based on the dispersion.

The carbon content of the surface-modified metal oxide powder is preferably 3-25 wt %.

The pH of the liquid phase of the dispersion is preferably 8-12, particularly preferably 9-11.

The surface-modified metal oxide powder may be in the form of isolated individual particles and/or in the form of aggregated particles. In the case of aggregated particles the median particle diameter refers to the dimension of the aggregate.

It has been found that the best results in terms of salt and temperature stability of the dispersion are obtained with a surface-modified metal oxide powder which in the dispersion has a median particle diameter $d_{50}$ of 40-200 nm. The median particle diameter may be determined with the customary methods of light scattering for the determination of particle size distributions in dispersions known to those skilled in the art.

The surface-modified metal oxide present in the dispersion according to the invention is inter alia characterized in that the surface modification comprises a hydrocarbon radical bonded to an Si atom via a C atom. This hydrocarbon radical is to be chosen such that the surface-modified mixed oxide exhibits hydrophilic properties in the dispersion. This depends for example on the number of carbon atoms in the hydrocarbon radical and on the presence of functional hydrophilic groups, such as hydroxyl, ether, amine or carboxyl groups. The hydrocarbon radical is preferably interrupted by one or more heteroatoms. O or N is particularly preferred as the heteroatom.

It is preferable when a surface modification is selected from the group consisting of Si—$(CH_2)_n$—$Y_m$—R, wherein Si is the Si atom bonded to a hydrocarbon radical via a C atom and n=1, 2 or 3 and m=0 or 1

R is a radical which does not impart hydrophobic properties and preferably in the case where m=1

R=—H, —$CH_3$, —$C_2H_5$, —OH, —$OCH_3$, —$OC_2H_5$, —C(=O)$OCH_3$, —C(=O)$OC_2H_5$, —O—C(=O)$CH_3$, —O—C(=O)$CH_3$, —O—C(=O)CH=$CH_2$, —O—C(=O)CH=CH($CH_3$), —C(=O)$CH_3$, —C(=O)H, $NH_2$;

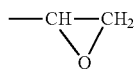

and in the case where m=0, R represents the abovementioned radicals but without —H, —$CH_3$, —$C_2H_5$.

Y=—$(OCR^1R^2$—$CR^3R^4)_o$—, o=1-30, $R^1$, $R^2$, $R^3$, $R^4$=independently of one another H or $CH_3$, particularly preferably o=5-15 and $R^1$, $R^2$, $R^3$, $R^4$=H;

—$(OCR^1R^2$—$CR^3R^4$—$CR^6R^6)_p$—, p=1-30, $R^1$, $R^2$, $R^3$, $R^4$, $R^5$, $R^6$=independently of one another H or $CH_3$, —$NHCH_2CH_2O$—, —$NH(CH_2)_2NH(CH_2)_2$—, —$NH(CH_2)_2NH(CH_2)_2$— or is a mixture of the abovementioned radicals R and Y.

It is likewise conceivable for Y to comprise branched polyethylene glycols. Here, R and at least one of the $R^1$-$R^6$ radicals represents an —$(OCH_2$—$CH_2)_r$ moiety where r=5-15.

The dispersion according to the invention may contain small amounts, less than 100 ppm, of customary dispersants. However, the presence of dispersants is not desired in the context of the present invention. The stabilizing effect of the dispersion according to the invention derives solely from the surface-modified metal oxide powder.

The invention further provides a process for producing the aqueous dispersion comprising dispersing a metal oxide powder selected from the group consisting of $TiO_2$, $ZrO_2$, $SiO_2$, $Al_2O_3$, $Fe_2O_3$, $Fe_3O_4$, $Sb_2O_3$, $WO_3$, $CeO_2$ and mixed oxides thereof having hydroxyl groups at the surface of the particles in an aqueous solvent and subsequently adding a surface modifying agent, reacting the mixture and optionally removing the hydrolysis product, wherein the surface modifying agent is obtained when a) a compound in which an Si atom is bonded to a hydrocarbon radical via a C atom and the Si atom is further bonded to one or more hydroxyl groups, alkoxy groups, halide groups or mixtures thereof and b) at least one metal compound selected from the group consisting of the metal alkoxides and metal acetylacetonates of aluminum, titanium and zirconium and also sodium aluminate, wherein c) the M/Si molar ratio of the surface modification is 1:2-1:20, are mixed and optionally subjected to thermal treatment and optionally subjected to pH adjustment.

The amount of the surface-modifying agent is guided by the desired ratio of silica to surface-modifying agent. The carbon fraction of the surface-modified silica has proven a suitable variable. Said fraction is preferably 3-25 wt %. The amount of hydroxyl groups, alkoxy groups or halide groups eliminated in the course of the hydrolysis must be taken into account.

Numerous methods of dispersing are available to those skilled in the art. To produce finely divided dispersions, apparatuses such as for example ultrasound probes, ball mills, stirred ball mills, rotor/stator machines, planetary kneaders/mixers or high-energy mills or combinations thereof are available. Thus for example a preliminary dispersion may be prepared using a rotor/stator system which in a subsequent step is subjected to further milling by means of a high-energy mill. This combination makes it possible, for example, to produce extra fine dispersions having a particle diameter of 200 nm or less. In the case of a high-energy mill, a preliminary dispersion under high pressure is divided into two or more streams, which are then decompressed through a nozzle and impinge exactly on one another.

It has proven advantageous to proceed directly from an aqueous dispersion of the metal oxide.

The mixture is generally reacted by adjusting the pH to 11 or more, subjecting the mixture to thermal treatment at a temperature of 50-95° C. over a period of 1-30 minutes and then optionally adjusting the pH to 8-10.

The BET surface area of the metal oxide powder or of the mixed metal oxide powder is preferably 40-500 m$^2$/g, particularly preferably 80-300 m$^2$/g. The BET surface area is determined in accordance with DIN 66131. In a particular embodiment a pyrogenic metal oxide powder or a pyrogenic mixed metal oxide powder is employed.

A pyrogenic mixed silicon-aluminum oxide powder has proven particularly advantageous. Commercially available examples are AEROSIL® MOX 80, Evonik Industries, having a BET surface area of 60-100 m$^2$/g and an aluminum oxide content of 0.3-1.3 wt % and AEROSIL® MOX 170, Evonik Industries, having a BET surface area of 140-200 m$^2$/g and an aluminum oxide content of 0.3-1.3 wt %. Both pyrogenic mixed silicon-aluminum oxide powders may be employed with preference. AEROSIL® MOX 170 is particularly preferred.

It is additionally possible to employ the pyrogenic mixed silicon-aluminum oxide powder disclosed in EP-A-995718. Said powder is obtained by reacting a vaporous silicon dioxide precursor and an aluminum chloride solution in a flame. The fine distribution of aluminum chloride in the aerosol and during the genesis of the oxide in the gas phase results in substantially homogeneous incorporation of the aluminum.

It is likewise possible to employ the pyrogenic mixed silicon-aluminum oxide powder disclosed in EP-A-2500090 where the weight ratio of $(Al_2O_3/SiO_2)_{ttl}$ in the overall particle is 0.002 to 0.05, and the $(Al_2O_3/SiO_2)_{surface}$ weight ratio of the particles in a layer close to the surface is lower than in the overall particle. The aluminum oxide concentration at the surface has thus been reduced further.

The compound in which an Si atom is bonded to a hydrocarbon radical via a C atom and the Si atom is further bonded to one or more hydroxyl groups, alkoxy groups, halide groups or mixtures thereof is preferably selected from the group consisting of $X_{4-a}[Si-(CH_2)_n-Y_m-R]_a$, where a=1, 2 or 3; preferably a=1; n=1, 2 or 3; m=0 or 1,
X=H, OH, OCH$_3$, OC$_2$H$_5$, OCH$_2$CH$_2$H$_3$, OCH(CH$_3$)$_2$; Cl,
R is a radical which does not impart hydrophobic properties and preferably in the case where m=1
R=—H, —CH$_3$, —C$_2$H$_5$, —OH, —OCH$_3$, —OC$_2$H$_5$, —C(=O)OCH$_3$, —C(=O)OC$_2$H$_5$, —O—C(=O)CH$_3$, —O—C(=O)CH$_3$, —O—C(=O)CH=CH$_2$, —O—C(=O)CH=CH(CH$_3$), —C(=O)CH$_3$, —C(=O)H, NH$_2$;

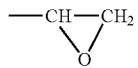

and in the case where m=0, R represents the abovementioned radicals but without —H, —CH$_3$, —C$_2$H$_5$.
Y=—(OCR$^1$R$^2$—CR$^3$R$^4$)$_o$—, o=1-30, R$^1$, R$^2$, R$^3$, R$^4$=independently of one another H or CH$_3$, particularly preferably o=5-15 and R$^1$, R$^2$, R$^3$, R$^4$=H;
—(OCR$^1$R$^2$—CR$^3$R$^4$—CR$^5$R$^6$)$_p$—, p=1-30, R$^1$, R$^2$, R$^3$, R$^4$, R$^5$, R$^6$=independently of one another H or CH$_3$, —NHCH$_2$CH$_2$O—, —NH(CH$_2$)$_2$NH(CH$_2$)$_2$—, —NH(CH$_2$)$_2$NH(CH$_2$)$_2$—
or is a mixture of the abovementioned radicals R and Y.

It is likewise conceivable for Y to comprise branched polyethylene glycols. Here, R and at least one of the R$^1$-R$^6$ radicals represents an —(OCH$_2$—CH$_2$)$_r$ moiety where r=5-15.

The compound in which an Si atom is bonded to a hydrocarbon radical via a C atom and the Si atom is further bonded to one or more hydroxyl groups, alkoxy groups, halide groups or mixtures thereof may particularly preferably be selected from the group consisting of (CH$_3$O)$_3$Si(CH$_2$)$_3$—OCH$_3$, (CH$_3$O)$_3$Si(CH$_2$)$_3$—(OCH$_2$CH$_2$)$_3$—OCH$_3$, (CH$_3$O)$_3$Si(CH$_2$)$_3$—(OCH$_2$CH$_2$)$_{6-9}$—OCH$_3$, (CH$_3$O)$_3$Si(CH$_2$)$_3$—(OCH$_2$CH$_2$)$_{9-12}$—OCH$_3$, (CH$_3$O)$_3$Si(CH$_2$)$_3$—(OCH$_2$CH$_2$)$_{21-24}$—OCH$_3$ and (CH$_3$CH$_2$O)$_3$Si(CH$_2$)$_3$—(OCH$_2$CH$_2$)$_{8-12}$OH.

2-[Methoxy(polyethyleneoxy)$_{6-9}$propyl]trimethoxysilane is very particularly preferred.

The compound in which an Si atom is bonded to a hydrocarbon radical via a C atom and the Si atom is further bonded to one or more hydroxyl groups, alkoxy groups, halide groups or mixtures thereof may further be selected from the group consisting of (RO)$_3$Si—(CH$_2$)$_3$—NH$_2$, (RO)$_3$Si—(CH$_2$)$_3$—CH—CH$_2$—NH$_2$, (RO)$_3$Si—(CH$_2$)$_3$—NH—(CH$_2$)$_2$—NH$_2$, (RO)$_3$Si—(CH$_2$)$_3$—NH—(CH$_2$)$_2$NH(CH$_2$)—NH$_2$, (RO)$_3$Si—(CH$_2$)$_3$—N—[(CH$_2$)$_2$NH(CH$_2$)—NH$_2$]$_2$, R=CH$_3$, C$_2$H$_5$.

An easily redispersible, surface-modified powder can be obtained from the dispersion according to the invention by removal of the liquid phase, for example by spray drying. This powder can be incorporated into an aqueous phase with a low input of energy, for example by stirring, without appreciable aggregation of the particles. The median particle diameter $d_{50}$ in this dispersion may be 40-200 nm.

The invention further provides an aqueous dispersion obtainable by dispersing a metal oxide powder selected from the group consisting of TiO$_2$, ZrO$_2$, SiO$_2$, Al$_2$O$_3$, Fe$_2$O$_3$, Fe$_3$O$_4$, Sb$_2$O$_3$, WO$_3$, CeO$_2$ and mixed oxides thereof having hydroxyl groups at the surface of the particles in an aqueous solvent and subsequently adding a surface modifying agent, reacting the mixture and optionally removing the hydrolysis product,
wherein the surface modifying agent is obtained when
a) a compound in which an Si atom is bonded to a hydrocarbon radical via a C atom and the Si atom is further bonded to one or more hydroxyl groups, alkoxy groups, halide groups or mixtures thereof and
b) at least one metal compound selected from the group consisting of at least one metal compound selected from the group consisting of metal alkoxides and metal acetylacetonates of aluminum, titanium and zirconium and also sodium aluminate, wherein
c) the M/Si molar ratio of the surface modification is 1:2-1:20,
are mixed and optionally subjected to thermal treatment.

The invention further provides a specific surface-modified mixed oxide powder comprising silicon and aluminum, in which
a) the Al$_2$O$_3$/SiO$_2$ weight ratio is 0.1:99.9-5:95,
b) the surface modification
   b1) comprises silicon atoms and aluminum atoms and
   b2) the silicon atoms are at least partly bonded to a hydrocarbon radical via a C atom and
   b3) the Al/Si molar ratio of the surface modification is 1:2-1:20.

The silicon atoms which are at least partly bonded to a hydrocarbon radical via a C atom are a constituent of the radical Si—(CH$_2$)$_n$—Y$_m$—R and
R is a radical which does not impart hydrophobic properties and preferably in the case where m=1
R=—H, —CH$_3$, —C$_2$H$_5$, —OH, —OCH$_3$, —OC$_2$H$_5$, —C(=O)OCH$_3$, —C(=O)OC$_2$H$_5$, —O—C(=O)CH$_3$,

—O—C(=O)CH₃, —O—C(=O)CH=CH₂, —O—C(=O)CH=CH(CH₃), —C(=O)CH₃, —C(=O)H, NH₂;

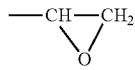

and in the case where m=0, R represents the abovementioned radicals but without —H, —CH₃, —C₂H₅
Y=—(OCR¹R²—CR³R⁴)ₒ—, o=1-30, R¹, R², R³, R⁴=independently of one another H or CH₃, particularly preferably o=5-15 and R¹, R², R³, R⁴=H;
—(OCR¹R²—CR³R⁴—CR⁵R⁶)ₚ—, p=1-30, R¹, R², R³, R⁴, R⁵, R⁶=independently of one another H or CH₃, —NHCH₂CH₂O—, —NH(CH₂)₂NH(CH₂)₂—, —NH(CH₂)₂NH(CH₂)₂—
or is a mixture of the abovementioned radicals R and Y.

It is likewise conceivable for Y to comprise branched polyethylene glycols. Here, R and at least one of the R¹-R⁶ radicals represents an —(OCH₂—CH₂)ᵣ moiety where r=5-15.

The BET surface area of the surface-modified metal oxide powder is preferably 40-500 m²/g, particularly preferably 80-300 m²/g. The BET surface area is determined according to DIN 66131.

The invention further provides for the use of the dispersion according to the invention and of the surface-modified mixed silicon-aluminum oxide powder according to the invention respectively as a constituent of pharmaceutical preparations, cosmetic preparations, water-based paints and coatings, of cleaning products, of dishwashing detergents and of coloured coating slips in the paper industry.

EXAMPLES

Salt Stability at 60° C.

28.500 g of NaCl, 0.220 g of NaHCO₃, 4.066 g of Na₂SO₄, 1.625 g of CaCl₂×2H₂O, 3.162 g of MgCl₂×6H₂O, 0.024 g of SrCl₂×6H₂O and 0.721 g of KCl are dissolved in 900 g of deionized water (DI water) and the solution made up to 1 litre with DI water.

99.5 g of this solution are initially charged into a 125 ml wide-necked bottle made of NALGENE® FEP (tetrafluoroethylene-hexafluoropropylene copolymer; Thermo Scientific), 0.5 g of the dispersion under test is added and the mixture is homogenized by shaking. The mixture is stored in a drying cabinet at 60° C. and the occurrence of a precipitate is visually monitored.

Salt Stability at 90° C.

99.5 g of a NaCl solution (3 wt %) are initially charged into a 125 ml wide-necked bottle made of NALGENE® FEP (tetrafluoroethylene-hexafluoropropylene copolymer; Thermo Scientific), 0.5 g of the dispersion under test is added and the mixture is homogenized by shaking. The mixture is stored in a drying cabinet at 90° C. and the occurrence of a precipitate is visually monitored.

Input Materials

Dispersion of mixed silicon-aluminum oxide AEROSIL® MOX 170
The powder has the following properties:
99 wt % silicon dioxide, 1 wt % aluminum oxide. The BET surface area is 173 m²/g. $(Al_2O_3/SiO_2)_{ttl}/(Al_2O_3/SiO_2)_{surface}$=0.9.

A 100 l stainless steel mixing vessel was initially charged with 37 kg of water. Subsequently, under shear conditions (Ystral Conti-TDS 3 (stator slots: 4 mm ring and 1 mm ring, rotor-stator gap about 1 mm), an initial 10 kg of AEROSIL® MOX 170 are aspirated. The remaining 5 kg were aspirated stepwise in amounts of about 1 kg each time. After addition was complete the mixture was sheared at 3000 rpm for a further 30 min. To grind any residual proportions of coarse particles this predispersion was passed in two runs through a Sugino Ultimaizer HJP-25050 high-energy mill at a pressure of 2500 bar with diamond nozzles of 0.25 mm in diameter, thus subjecting it to further intensive grinding. The concentration of AEROSIL® MOX 170 is 20 wt %. The median particle diameter $d_{50}$ is determined by static light scattering (LA-950, Horiba Ltd., Japan) as 112 nm.

LUDOX® SM 30, Grace, is an aqueous, NaOH-stabilized, colloidal silica dispersion having a particle size of 8 nm and an SiO₂ content of 30 wt %.

LUDOX® HS 40, Grace, is an aqueous, NaOH-stabilized, colloidal silica dispersion having a particle size of 12 nm and an SiO₂ content of 40 wt %.

LUDOX® CL, Grace, is an aqueous dispersion of Al-coated, colloidal silica having a particle size of 22 nm. The pH is 3.5-4.5, the solids content 39-43 wt %.

Surface Modifying Agents
OM1: 2-[methoxy(polyethyleneoxy)₆₋₉ propyl]trimethoxysilane
OM2: aluminum isopropoxide
Water: this is fully deionized water.
Aqueous sodium hydroxide solution: 25 wt % NaOH
hydrochloric acid: 20 wt % HCl
Production of Mixtures of OM1 and OM2
Mixture 1: Al/Si ratio=1:6.5
20 g of OM2 are added to 150 g of OM1 and the mixture is heated to 70° C. while stirring. After cooling, insoluble components are removed by centrifuging. RFA analysis of the ash shows 11.5 wt % Al₂O₃ and 88.5 wt % SiO₂.
This corresponds to an Al/Si molar ratio of 1:6.5.
Mixture 2: Al/Si ratio=1:13: further proportions of OM1 are added to mixture 1.
Mixture 3: Al/Si ratio=1:26: further proportions of OM1 are added to mixture 1.

Example 1 (Inventive)

10.25 g of mixture 1 are slowly added to 40 g of the dispersion of mixed silicon-aluminum oxide with stirring. There is an initial viscosity increase though this falls again upon further addition. The mixture is then adjusted to pH 11 with aqueous sodium hydroxide solution with stirring and the mixture is heated to 90° C. After 10 minutes at 90° C. the mixture is left to cool to room temperature and the mixture is adjusted to pH 9 with hydrochloric acid.

$d_{50}$=123 nm; salt stability at 90° C. is 3 weeks (precipitate visually perceptible).

Example 2 (Inventive)

10.25 g of mixture 2 are slowly added to 40 g of the dispersion of mixed silicon-aluminum oxide with stirring. There is an initial viscosity increase though this falls again upon further addition. The mixture is then adjusted to pH 11 with aqueous sodium hydroxide solution with stirring and the mixture is heated to 90° C. After 10 minutes at 90° C. the mixture is left to cool to room temperature and the mixture is adjusted to pH 9 with hydrochloric acid.

$d_{50}$=122 nm; salt stability at 90° C. is 2 weeks.

Example 3 (Comparative)

10.25 g of mixture 3 are slowly added to 40 g of the dispersion of mixed silicon-aluminum oxide with stirring.

There is an initial viscosity increase though this falls again upon further addition. The mixture is then adjusted to pH 11 with aqueous sodium hydroxide solution with stirring and the mixture is heated to 90° C. After 10 minutes at 90° C. the mixture is left to cool to room temperature and the mixture is adjusted to pH 9 with hydrochloric acid. Salt stability at 90° C. is just a few hours.

Example 4 (Comparative)

10.25 g of OM1 are added slowly with stirring to 40 g of the dispersion of mixed silicon-aluminum oxide. There is an initial viscosity increase though this falls again upon further addition. The mixture is then adjusted to pH 11 with aqueous sodium hydroxide solution with stirring and the mixture is heated to 90° C. After 10 minutes at 90° C. the mixture is left to cool to room temperature and the mixture is adjusted to pH 9 with hydrochloric acid. Salt stability at 90° C. is just a few hours.

Example 5 (Comparative)

4.3 g of OM1 are added dropwise over 3 hours at 80° C. with stirring to 100 g of a LUDOX® 30 SM dispersion diluted with deionized water to 10 wt %. The mixture is stirred at 80° C. for a further 6 hours. The salt stability at 60° C. is 1 day.

Example 6 (Comparative)

30 g of OM1 are added to 249 g of LUDOX® HS 40. The dispersion is heated to 80° C. and stirred at this temperature for 16 hours. The salt stability at 60° C. is 1 day.

Example 7 (Comparative)

26.7 g of LUDOX® CL are diluted to 20 wt % with 13.3 g of DI water. 13.0 g of OM1 are added to this sol slowly and with stirring. The mixture is then adjusted to pH 11 with aqueous sodium hydroxide solution with stirring and the mixture is heated to 90° C. After 10 minutes at 90° C. the mixture is cooled and adjusted to pH 9 with hydrochloric acid. The salt stability at 60° C. is 2 days.

The inventive dispersion of examples 1 and 2 exhibit good salt stability at a temperature of 90° C.

In example 3 (comparative) the proportion of $SiO_2$ in the surface modification is increased compared to inventive examples 1 and 2.

In examples 4-6 (comparative) the surface modification contains no Al. These dispersions exhibit markedly lower stability.

In example 7 (comparative) the surface modification contains only Al. This dispersion too exhibits a markedly lower stability.

Example 9 (Inventive): Redispersible Powder

A dispersion produced according to example 1 is used to generate an easily redispersible powder with the aid of a Mini Spray Dryer B-290 from BÜCHI Labortechnik GmbH using nitrogen as the hot gas medium. Stirring-in using a magnetic stirrer affords a $d_{50}$ of 155 nm, with a dissolver after 5 minutes at 2000 rpm a $d_{50}$ of 136 nm and with an ULTRA-TURRAX® T 25, IKA®-Werke GmbH & CO. KG after a minute at 9000 rpm a $d_{50}$ of 130 nm.

The invention claimed is:
1. An aqueous dispersion containing a hydrophilic metal oxide powder comprising a metal oxide and a surface modification of the metal oxide, wherein:
 a) the metal oxide is a mixed aluminum-silicon oxide; and
 b) the surface modification comprises:
  b1) silicon and Al atoms;
  b2) wherein the silicon atoms are at least partly bound to a hydrocarbon radical by a C atom; and
  b3) wherein the Al/Si molar ratio of the surface modification is 1:2-1:20;
wherein the surface modification has the formula Si—$(CH_2)_n$—$Y_m$—R, wherein Si is the Si atom bonded to a hydrocarbon radical via a C atom, n=1, 2 or 3 and m=0 or 1;
wherein the $Al_2O_3/SiO_2$ weight ratio in the surface-modified metal oxide powder is 0.1:99.9-5:95;
and wherein:
when m=1: R=—H, —$CH_3$, —$C_2H_5$, —OH, —$OCH_3$, —$OC_2H_5$, —C(=O)$OCH_3$, —C(=O)$OC_2H_5$, —O—C(=O)$CH_3$, —O—C(=O)CH=$CH_2$, —O—C(=O)CH=CH($CH_3$), —C(=O)$CH_3$, —C(=O)H, $NH_2$; or

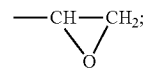

when m=0: R=—OH, —$OCH_3$, —$OC_2H_5$, —C(=O)$OCH_3$, —C(=O)$OC_2H_5$, —O—C(=O)$CH_3$, —O—C(=O)CH=$CH_2$, —O—C(=O)CH=CH($CH_3$), —C(=O)$CH_3$, —C(=O)H, or $NH_2$; and
Y=—($OCR^1R^2$—$CR^3R^4$)$_o$—, where o=1-30, and $R^1$, $R^2$, $R^3$, $R^4$=independently of one another H or $CH_3$, or —($OCR^1R^2$—$CR^3R^4$—$CR^5R^6$)$_p$—, where p=1-30, $R^1$, $R^2$, $R^3$, $R^4$, $R^5$, $R^6$=independently of one another H or $CH_3$, —$NHCH_2CH_2O$—, —$NH(CH_2)_2NH(CH_2)_2$—, or —$NH(CH_2)_2NH(CH_2)_2$—.

2. The aqueous dispersion of claim 1, wherein the proportion of water is 50-90 wt % and the proportion of surface-modified metal oxide powder is 10-50 wt %.

3. The aqueous dispersion of claim 1, wherein Y=—($OCR^1R^2$—$CR^3R^4$)O—, o=5-15 and $R^1$, $R^2$, $R^3$, $R^4$=H.

4. The aqueous dispersion of claim 3, wherein the proportion of water is 50-90 wt % and the proportion of surface-modified metal oxide powder is 10-50 wt %.

5. The aqueous dispersion of claim 1, wherein no more than 100 ppm of dispersants are present.

6. The aqueous dispersion of claim 1, wherein the $Al_2O_3/SiO_2$ weight ratio in the surface-modified metal oxide powder is in the range 0.2:99.8-3:97.

7. The aqueous dispersion of claim 1, wherein the dispersion has a median particle diameter $d_{50}$ of 40-200 nm.

8. A surface-modified mixed aluminum-silicon oxide powder,
wherein:
 a) the $Al_2O_3/SiO_2$ weight ratio is 0.1:99.9-5:95;
 b) the surface modification:
  b1) comprises silicon atoms and aluminum atoms;
  b2) comprises the formula Si—$(CH_2)_n$—$Y_m$—R, wherein Si is the Si atom bonded to a hydrocarbon radical via a C atom, n=1, 2 or 3 and m=0 or 1; and
  b3) comprises an Al/Si molar ratio of 1:2-1:20; and
  wherein:
when m=1: R=—H, —$CH_3$, —$C_2H_5$, —OH, —$OCH_3$, —$OC_2H_5$, —C(=O)$OCH_3$, —C(=O)$OC_2H_5$, —O—C(=O)CH$_3$, —O—C(=O)CH=CH$_2$, —O—C(=O)CH=CH(CH$_3$), —C(=O)CH$_3$, —C(=O)H, NH$_2$, or

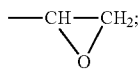

when m=0: R=—OH, —OCH$_3$, —OC$_2$H$_5$, —C(=O)OCH$_3$, —C(=O)OC$_2$H$_5$, —O—C(=O)CH$_3$, —O—C(=O)CH=CH$_2$, —O—C(=O)CH=CH(CH$_3$), —C(=O)CH$_3$, —C(=O)H, or NH$_2$; and Y=—(OCR$^1$R$^2$—CR$^3$R$^4$)O—, where o=1-30, and R$^1$, R$^2$, R$^3$, R$^4$=independently of one another H or CH$_3$, or —(OCR$^1$R$^2$—CR$^3$R$^4$—CR$^5$R$^6$)$_p$—, where p=1-30, R$^1$, R$^2$, R$^3$, R$^4$, R$^5$, R$^6$=independently of one another H or CH$_3$, —NHCH$_2$CH$_2$O—, —NH(CH$_2$)$_2$NH(CH$_2$)$_2$—, or —NH(CH$_2$)$_2$NH(CH$_2$)$_2$—.

9. The surface-modified mixed aluminum-silicon oxide powder of claim 8, wherein Y=—(OCR$^1$R$^2$—CR$^3$R$^4$)$_o$—, o=5-15 and R$^1$, R$^2$, R$^3$, R$^4$=H.

10. The surface-modified mixed aluminum-silicon oxide powder of claim 8, wherein the Al$_2$O$_3$/SiO$_2$ weight ratio in the surface-modified metal oxide powder is 0.2:99.8-3:97.

11. A process for producing the aqueous dispersion of claim 1, comprising: dispersing in an aqueous solvent a powder comprising mixed aluminum-silicon oxides and having hydroxyl groups at the surface of particles in the powder; subsequently adding a surface modifying agent; reacting the mixture; and optionally removing the hydrolysis product, wherein the surface modifying agent is obtained by mixing:

a) a compound with the structure of X$_{4-a}$[Si—(CH$_2$)$_n$—Y$_m$—R]$_a$ with b) at least one metal compound selected from the group consisting of aluminum alkoxides, aluminum acetylacetonates, and sodium aluminate;

wherein
a=1, 2 or 3;
n=1, 2 or 3;
m=0 or 1, wherein:
when m=1: R=—H, —CH, —C$_2$H$_5$, —OH, —OCH, —OC$_2$H$_5$, —C(=O)OCH$_3$, —C(=O)OC$_2$H$_5$, —O—C(=O)CH$_3$, —O—C(=O)CH=CH$_2$, —O—C(=O)CH=CH(CH$_3$), —C(=O)CH$_3$, —C(=O)H, NH$_2$; or

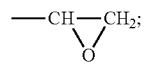

and when m=0: R=—OH, —OCH, —OC$_2$H$_5$, —C(=O)OCH$_3$, —C(=O)OC$_2$H$_5$, —O—C(=O)CH$_3$, —O—C(=O)CH=CH$_2$, —O—C(=O)CH=CH(CH$_3$), —C(=O)CH$_3$, —C(=O)H, or NH$_2$; and Y=—(OCR$^1$R$^2$—CR$^3$R$^4$)$_o$—, where o=1-30, and R$^1$, R$^2$, R$^3$, R$^4$=independently of one another H or CH, or —(OCR$^1$R$^2$—CR$^3$R$^4$—CR$^5$R$^6$)$_p$—, where p=1-30, R$^1$, R$^2$, R$^3$, R$^4$, R$^5$, R$^6$=independently of one another H or CH$_3$, —NHCH$_2$CH$_2$O—, —NH(CH$_2$)$_2$NH(CH$_2$)$_2$—, or —NH(CH$_2$)$_2$NH(CH$_2$)$_2$—.

12. The process of claim 11, wherein Y=—(OCR$^1$R$^2$—CR$^3$R$^4$)$_o$—, o=5-15 and R$^1$, R$^2$, R$^3$, R$^4$=H.

13. The process of claim 11, wherein the metal oxide powder is introduced in the form of an aqueous dispersion.

14. The process of claim 11, wherein the process comprises reacting the mixture by adjusting the pH to 11 or higher, subjecting the mixture to thermal treatment at a temperature of 50-95° C. over a period of 1-30 minutes and then optionally adjusting the pH to 8-10.

15. The process of claim 11, wherein a metal oxide powder produced by pyrogenic means is employed.

16. The process of claim 11, wherein X is selected from the group consisting of H, OH, OCH$_3$, OC$_2$H$_5$, OCH$_2$CH$_2$H$_3$, OCH(CH$_3$)$_2$, and Cl.

* * * * *

UNITED STATES PATENT AND TRADEMARK OFFICE
CERTIFICATE OF CORRECTION

PATENT NO. : 10,920,084 B2
APPLICATION NO. : 15/743242
DATED : February 16, 2021
INVENTOR(S) : Wolfgang Lortz et al.

Page 1 of 1

It is certified that error appears in the above-identified patent and that said Letters Patent is hereby corrected as shown below:

In the Claims

Column 10, Line 43 (Claim 3), "Y=—(OCR$^1$R$^2$—CR$^3$R$^4$)O—" is corrected to read:
--Y=—(OCR$^1$R$^2$—CR$^3$R$^4$)$_o$— --.

Column 11, Line 14 (Claim 8), "Y=—(OCR$^1$R$^2$—CR$^3$R$^4$)O—" is corrected to read:
--Y=—(OCR$^1$R$^2$—CR$^3$R$^4$)$_o$— --.

Column 12, Line 5 (Claim 11), "when m=1: R=—H, —CH, —C$_2$H$_5$, —OH, —OCH" is corrected to read:
--when m=1: R=—H, —CH$_3$, —C$_2$H$_5$, —OH, —OCH$_3$--.

Column 12, Line 16 (Claim 11), "when m=0: R=—OH, —OCH" is corrected to read:
--when m=0: R=—OH, —OCH$_3$--.

Column 12, Line 21 (Claim 11), "independently of one another H or CH" is corrected to read:
--independently of one another H or CH$_3$--.

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*